US011850296B2

(12) United States Patent
Viscogliosi et al.

(10) Patent No.: US 11,850,296 B2
(45) Date of Patent: Dec. 26, 2023

(54) HAIR DYEING COMPOSITION

(71) Applicant: DI VISCO, Saint Genis Laval (FR)

(72) Inventors: Sébastien Frédéric Viscogliosi, Lyons (FR); Isabel Garcia, Lyons (FR)

(73) Assignee: DI VISCO, Saint Genis Laval (FR)

( * ) Notice: Subject to any disclaimer, the term of this patent is extended or adjusted under 35 U.S.C. 154(b) by 0 days.

(21) Appl. No.: 17/616,743

(22) PCT Filed: Jun. 5, 2020

(86) PCT No.: PCT/FR2020/050958
§ 371 (c)(1),
(2) Date: Dec. 6, 2021

(87) PCT Pub. No.: WO2020/245546
PCT Pub. Date: Dec. 10, 2020

(65) Prior Publication Data
US 2022/0331215 A1 Oct. 20, 2022

(30) Foreign Application Priority Data
Jun. 7, 2019 (FR) ...................... 19/06053

(51) Int. Cl.
*A61Q 5/10* (2006.01)
*A61K 8/04* (2006.01)
(Continued)

(52) U.S. Cl.
CPC .................. *A61K 8/04* (2013.01); *A61K 8/34* (2013.01); *A61K 8/645* (2013.01); *A61K 8/65* (2013.01);
(Continued)

(58) Field of Classification Search
CPC . A61K 8/41; A61K 8/34; A61K 8/645; A61K 8/65; A61K 8/922; A61K 2800/43; A61K 8/362; A61K 8/44; A61K 8/442; A61K 8/26; A61K 8/19; A61K 8/447; A61K 8/466; A61K 8/4913; A61K 8/492;
(Continued)

(56) References Cited

U.S. PATENT DOCUMENTS 5,843,193 A 12/1998 Hawkins et al.
2001/0042276 A1* 11/2001 Kawasoe ................ A61K 8/26
8/405

(Continued)

FOREIGN PATENT DOCUMENTS

JP 4891449 B1 * 3/2012 ............... A61Q 5/10
KR 10-2009-0012647 A 2/2009
(Continued)

OTHER PUBLICATIONS

Database WPI Week 201508 Thomson Scientific, London, GB; AN2015-078396 XP002797036, & CN104177911 A (Bangbu Demei Filter Technologies Co Ltd) Dec. 3, 2014.
(Continued)

*Primary Examiner* — Eisa B Elhilo
(74) *Attorney, Agent, or Firm* — Oliff PLC

(57) ABSTRACT

A new composition for hair dyeing includes an amino acid, a protein, an alcohol, a mineral powder, a vegetable oil and a dye or a pigment, as well as a method for dyeing hair implementing said composition.

17 Claims, 8 Drawing Sheets

Photograph of the hair before treatment with the composition according to the invention

(51) Int. Cl.
*A61K 8/34* (2006.01)
*A61K 8/64* (2006.01)
*A61K 8/65* (2006.01)
*A61K 8/92* (2006.01)
*A61Q 5/06* (2006.01)

(52) U.S. Cl.
CPC .............. *A61K 8/922* (2013.01); *A61Q 5/065* (2013.01); *A61Q 5/10* (2013.01); *A61K 2800/43* (2013.01)

(58) Field of Classification Search
CPC .................... A61K 8/4946; A61K 8/64; A61K 2800/4324; A61K 8/72; A61K 2800/432; A61Q 5/065; A61Q 5/10; A61Q 5/06
USPC ........................................................... 8/405
See application file for complete search history.

(56) References Cited

U.S. PATENT DOCUMENTS

| | | | |
|---|---|---|---|
| 2007/0000070 A1* | 1/2007 | Vena | A61K 8/26 8/405 |
| 2009/0070945 A1* | 3/2009 | Nguyen | A61K 8/31 8/405 |
| 2011/0300083 A1* | 12/2011 | Yontz | A61P 31/10 424/769 |
| 2012/0102662 A1* | 5/2012 | Wood | A61Q 5/10 8/405 |
| 2016/0051458 A1* | 2/2016 | Dublanchet | A61Q 5/00 8/405 |

FOREIGN PATENT DOCUMENTS

| | | | | |
|---|---|---|---|---|
| KR | 20180056830 | * | 5/2018 | ............... A61Q 5/00 |
| RU | 2 677 275 C1 | | 1/2019 | |
| RU | 2 680 841 C1 | | 2/2019 | |
| WO | WO 2019012219 A1 | * | 1/2019 | ............... A61Q 5/04 |

OTHER PUBLICATIONS

Oct. 7, 2020 International Search Report issued in International Application No. PCT/FR2020/050958.

Oct. 7, 2020 Written Opinion report issued in International Patent Application No. PCT/FR2020/050958.

* cited by examiner

*Figure 1 – Photograph of the hair before treatment with the composition according to the invention*

Figure 2 – Photograph of the hair after treatment with the composition according to the invention

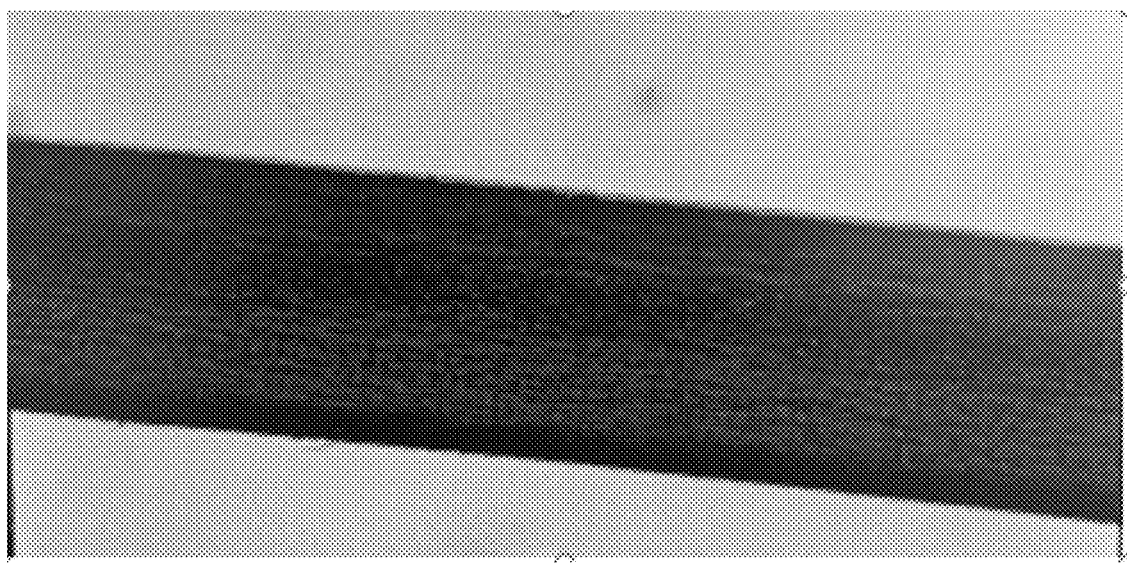
Figure 3 – Microscopic analysis of the structure of a hair after treatment with the composition according to the invention

Figure 4 – Photograph of the hair before treatment with the composition according to the invention

Figure 5 –Photograph of the hair during treatment with the composition according to the invention

Figure 6 – Photograph of the hair after treatment with the composition according to the invention

Figure 7 – Photograph of the hair after treatment with a composition according to the invention

Figure 8 –Photograph of the hair after treatment with an amino acid-free composition (Cream ref.)

HAIR DYEING COMPOSITION

The present invention relates to a novel composition for dyeing hair comprising an amino acid, a protein, an alcohol, a mineral powder, a vegetable oil and a dye or a pigment, as well as a method for dyeing hair implementing said composition.

In the field of hair care, coloring is a hairstyling technique that allows hair to be dyed permanently or temporarily.

Consumers wishing to dye their hair seek to obtain as natural dyeing as possible, hair with intense and shiny shades, but also a result that is durable over time by resisting in particular subsequent shampooing.

To change the dye of the hair in a long-lasting manner, chemical treatments called oxidation dyes are generally used. These treatments allow a pigmentary modification of the hair in its cortex by denaturing its melanin. Such treatments make it possible to achieve a dyed visual appearance, with a resistance for several months.

A first treatment for dyeing hair is thus based on the principle of the oxidative combination of two precursor components called base and coupler. The oxidation phase is carried out in the presence of hydrogen peroxide in a basic medium (pH between 9.5 and 10.5) with the implementation of ammoniacal solutions with a high fiber swelling capacity. This technology is particularly robust and compatible with all types of hair, but nevertheless requires rigorous compliance with the application conditions recommended by suppliers, particularly in terms of precautions for use and break time. They are also recognized as sensitizing and with high allergenic potential.

In addition, the base used consists of an aromatic diamine such as paraphenylenediamine (PPD), 1,4-piaminobenzene, p-phenylenediamine or p-aminoaniline. These components are known for their toxicity and prohibited in many cosmetics.

The coupler itself consists of a diphenol such as resorcinol, resorcin, 1,3-benzenediol, 1,3-dihydroxybenzene or m-dihydrobenzene. These components are also classified as toxic and dangerous.

A second treatment is based on the use of powders of tinctorial plants or henna. Although this is referred to as 'vegetable dyeing' and these treatments are considered more natural, they are not without consequences. Indeed, henna powders naturally contain traces of mercury and arsenic. In addition, the use of henna must in general be accompanied by the use of couplers such as sodium picramates and/or aromatic diamines (PPD) in order to obtain a visible result, more or less covering and long-lasting over time. Also, this treatment presents therefore a risk of toxicity by skin contact.

Furthermore, handling these treatments is tedious, with several applications spaced with break times ranging from 60 to 180 minutes being necessary to obtain an acceptable final result that is long-lasting over time.

Finally, these treatments are incompatible with any other chemical or organic treatment since they leave an impenetrable envelope around the fiber preventing the passage of any other product. The use of other treatments such as straighteners, perms or lightening can also be at the origin of the destruction of the hair due to the interaction of traces of mercury with the ammonia present therein.

New complementary treatments have been developed to provide hair dyeing without chemical damage. These treatments are based on the use of cationic dyes called direct dyes or basic dyes. These have a great affinity with keratin but do not have the ability to hold onto the hair in a long-lasting manner. Indeed, the cationic dye is deposited only on the periphery of the fiber so as not to damage the latter. Not very robust, this treatment quickly fades after a few shampoos.

Thus, at the date of the present invention, it is still necessary to develop a composition which makes it possible to dye the hair in an effective and long-lasting manner, which can be applied easily, and which does not deteriorate the quality of the hair.

Yet, It has now been found a composition allowing effective and long-lasting hair dyeing, according to an application method that is easy to implement, said composition preserving the quality of the hair.

The object of the present invention is therefore a composition for dyeing hair comprising:
  a proteinogenic amino acid selected from aspartic acid, glutamic acid, asparagine, carnitine, cysteine, glutamine, histidine, leucine, isoleucine, methionine, N-phenylalanine, proline, hydroxyproline, threonine, tryptophan, tyrosine, valine, glycine, alanine, serine, beta alanine, taurine, lysine and arginine or a salt thereof, acid or base, organic or inorganic;
  a protein;
  an alcohol;
  a mineral powder;
  a vegetable oil; and
  a dye or a pigment.

The composition according to the present invention allows effective and long-lasting hair dyeing, according to an easier application method (without oxidizing mixture to be carried out and without prolonged break time, the dye setting being instantaneous) and preserving the quality of the hair, in particular due to the absence of oxidation phase in a basic medium, of aromatic diamine, of diphenol and of ammonia. In addition, it allows the use of all types of dyes, in particular cationic dyes, direct dyes and vegetable dyes.

BRIEF DESCRIPTION OF THE DRAWINGS

FIG. 1 is a photograph of hair before treatment with the composition according to the invention.

FIG. 2 is a photograph of hair after treatment with the composition according to the invention.

FIG. 3 is a microscopic analysis of the structure of a hair after treatment with the composition according to the invention.

FIG. 4 is a photograph of hair before treatment with the composition according to the invention.

FIG. 5 is a photograph of hair during treatment with the composition according to the invention.

FIG. 6 is a photograph of hair after treatment with the composition according to the invention.

FIG. 7 is a photograph of hair after treatment with a composition according to the invention.

FIG. 8 is a photograph of hair after treatment with an amino acid-free composition.

In the context of the present invention:
  by "hair dyeing" it should be understood any treatment that transforms the natural hair dye in order to revive its shades or completely transform it;
  by "vegetable oil" it should be understood any fatty substance extracted from an oleaginous plant, that is to say a plant whose seeds, nuts or fruits contain lipids;
  by "protein" it should be understood any protein, heteroprotein or protein derivative such as a protein grafted onto a heteromolecule which may be silicone, a carbohydrate compound, a fatty acid or derivative, a surfactant of anionic, cationic or non-ionic or amphoteric nature, of variable size and shape, formed of one or several chain(s) loaded with amino acids and linked by peptide bonds. Preferably, the protein is of tertiary or quaternary structure;

by "$C_x$-$C_y$-alkyl" it should be understood a saturated, linear or branched hydrocarbon-based chain, and including from x to y carbon atoms;

by "alcohol" it should be understood any linear or branched carbon chain containing from 1 to 10 carbon atoms substituted by a hydroxyl group, an aminoalcohol, an aldol or a ketol. Preferably, "alcohol" denotes any linear or branched compound of formula $C_nH2_{n+1}OH$ wherein n is an integer comprised between 1 and 10;

by "polyol" it should be understood any $C_1$-$C_{10}$-alkyl group substituted by at least two hydroxyl groups. Preferably, by "polyol" it should be understood any compound selected from glycerin, propylene glycol, propan-1,3-diol or sorbitol;

by "mineral powder" it should be understood any powder prepared from a homogeneous natural solid in the form of salt, comprising one or several element(s) selected from magnesium ($Mg^{2+}$), calcium ($Ca^{26}$), sodium ($Na^+$) and potassium alum ($KAl(SO4)_{12}H_2O$);

by "dye" it should be understood any soluble substance consisting of a chromophore group and an auxochrome group. As examples of dyes, mention may in particular be made of azo dyes (or naphthol) such as benzimidazolone yellows or oranges; anthraquinone dyes such as alizarin, purpurine or indanthrene blue; indigo dyes such as indigo or indigo carmine; chlorine dyes such as chlorphylline; polymethine dyes such as rose or anthocyanin purple; acidic (or anionic) dyes such as patent blue V or fluorescine yellow; basic (or cationic) dyes such as malachite green, berberine yellow or fushin; direct (or substantive) dyes such as curcumin or cochineal; oxidation dyes requiring bases and couplers, such as paraphenylenediamine for the bases and 4-chloro-1 3-dinitrobenzene for the couplers; or even vegetable dyes such as madder or indigofera tinctoria; and by "pigment" it should be understood any dyeing substance of mineral or organic origin, natural or synthetic, insoluble in the medium that it dyes. As examples of pigments, mention may be made of inorganic pigments such as yellow ocher, red ocher or lapis lazuli; or organic pigments such as murex or sepia.

Furthermore, in the context of the present invention, and unless otherwise stated, the proportions expressed in % correspond to percentages by weight relative to the total weight of the entity considered.

The composition according to the present invention contains therefore an amino acid, a protein, an alcohol, a mineral powder, a vegetable oil and a dye or a pigment. Preferably, the present invention relates to a composition as described above having the following features, considered alone or in combination:

the amino acid is selected from aspartic acid, glutamic acid, asparagine, carnitine, cysteine, glutamine, histidine, methionine, proline, hydroxyproline, tyrosine, glycine, alanine, serine, beta alanine, taurine and arginine. Quite preferably, the amino acid is selected from glutamic acid, cysteine and arginine;

the composition contains from 0.1% to 20% of amino acid as defined above, preferably from 0.1% to 5% of amino acid as defined above, more preferably from 0.1% to 3% amino acid as defined above;

the protein is selected from optionally hydrolyzed creatine, optionally hydrolyzed keratin, optionally hydrolyzed wheat protein, optionally hydrolyzed silk protein, optionally hydrolyzed vegetable keratin, optionally hydrolyzed soy protein, optionally hydrolyzed collagen, optionally hydrolyzed elastin, optionally hydrolyzed pea protein, optionally hydrolyzed rice protein, optionally hydrolyzed conchioline protein and optionally hydrolyzed whey protein.

More preferably, the protein is selected from optionally hydrolyzed creatine, optionally hydrolyzed keratin, optionally hydrolyzed silk protein, optionally hydrolyzed vegetable keratin, optionally hydrolyzed soy protein, optionally hydrolyzed collagen, optionally hydrolyzed elastin, optionally hydrolyzed pea protein, optionally hydrolyzed rice protein, optionally hydrolyzed conchiolin protein and optionally hydrolyzed whey protein.

Quite preferably, the protein is selected from creatine, keratin, optionally hydrolyzed silk protein and optionally hydrolyzed soy protein;

the composition contains from 0.1% to 20% of protein as defined above, more preferably from 0.1% to 10% of protein as defined above, quite preferably from 0.1% to 5% of protein as defined above;

the alcohol is selected from butanol, isopropanol, ethanol and benzyl alcohol. More preferably, the alcohol is selected as being ethanol or benzyl alcohol;

the composition contains from 0.5% to 20% of alcohol as defined above, more preferably from 0.5% to 10% of alcohol as defined above, quite preferably from 0.5% to 4% of alcohol as defined above;

the vegetable oil contains at least 1% of chamazulene or carboxylic acids. More preferably, the vegetable oil is selected from sweet almond oil, olive oil, argan oil, matricaria chamomile oil, roman chamomile oil, Haarlem oil, babassu oil, broccoli oil, avocado oil, linseed oil, apricot oil, cucumber oil, black seed oil, Brazil nut oil, grape seed oil, shea olein, sesame oil and tomato oil. Quite preferably, the vegetable oil is seleced as either matricaria chamomile oil or roman chamomile oil;

the composition contains from 1% to 15% of vegetable oil as defined above, more preferably from 1% to 10% of vegetable oil as defined above, quite preferably from 1% to 8% of vegetable oil as defined above;

the mineral powder contains at least 1% of potassium or aluminum potassium disulphate.

Preferably, the mineral powder is selected from kaolin powder, tartaric acid powder, alum powder, calcium carbonate powder, potassium carbonate powder, tara powder, titanium oxalate, magnesium powder. Quite preferably, the mineral powder is selected as being alum powder or tartaric acid powder;

the composition contains from 0.1 to 20% of mineral powder as defined above, more preferably from 0.1 to 10% of mineral powder as defined above, quite preferably from 0.1 to 5% of mineral powder as defined above;

the dyes are selected from oxidation dyes, cationic dyes, vegetable dyes. More preferably, the dyes are selected from cationic dyes and vegetable dyes. Quite preferably, the dyes are selected as being cationic dyes;

the pigments are selected as being inorganic pigments;

the composition contains from 0.1 to 10% of dye or pigment as defined above, more preferably from 0.1 to 8% of dye or pigment as defined above, quite preferably 0.1 to 5% of dye or pigment as defined above; and/or the composition also contains a polyol.

The composition according to the invention is in the form of a single ready-to-use composition. This can be in the form of cream, gel, oil-in-water or water-in-oil emulsion, hair lotion or shampoo. Preferably, the composition according to the invention is in the form of a cream.

The composition according to the present invention, whether it is in the form of cream, emulsion, lotion or shampoo, can be applied according to any method known to those skilled in the art.

Preferably, the composition according to the present invention is applied according to the method comprising the following steps:
 applying the composition according to the invention directly to dry hair,
 leaving to act for a period that could vary from 5 minutes to 30 minutes; and
 rinsing the hair with water;

The method according to the present invention can also be supplemented by:
 applying a shampoo after rinsing the hair; and/or
 applying a conditioner balm or a no-rinse-treatment.

The method according to the present invention can be easily implemented and allows effective and long-lasting hair dyeing without the use of ammonia, hydrogen peroxide, base or coupler, all in a medium with an acidic pH of 5.5, thereby preserving the quality of the hair.

In addition, the composition according to the present invention can also be used to dye the eyelashes or eyebrows.

The present invention is illustrated in a nonlimiting manner by the following examples.

Example 1

Composition according to the invention

A ready-to-use dyeing cream comprising an amino acid, a protein, an alcohol, a mineral powder and a dye, the composition of which is reported in the following Table 1, is prepared.

TABLE 1

| Dyeing Cream | |
| --- | --- |
| Ingredients | Amount (% w/w) |
| Glutamic acid (amino acid) | 0.50 |
| Arginine (amino acid) | 0.50 |
| Cysteine (amino acid) | 0.10 |
| Hydrolyzed keratin (protein) | 1 |
| Hydrolyzed elastin (protein) | 0.80 |
| Hydrolyzed collagen (protein) | 0.40 |
| Cetearyl alcohol (alcohol) | 4.5 |
| Benzyl alcohol (alcohol) | 1.67 |
| Potassium alum (mineral powder) | 2 |
| Matricaria chamomile oil (vegetable oil) | 2 |
| Babassu oil (vegetable oil) | 1 |
| Wheat germ oil (vegetable oil) | 2 |
| Basic red 51 (cationic dye) | 2.59 |
| Titanium dioxide (mineral pigment) | 0.50 |
| Mica powder (mineral pigment) | 0.06 |
| Shea Butter | 4 |
| Cetrimonium chloride | 6.85 |
| Decyl glucoside | 1 |
| Propylene glycol | 1 |
| Guar hydroxypropyltrimonium chloride | 1 |
| Behentrimonium methosulfate | 0.50 |

TABLE 1-continued

| Dyeing Cream | |
| --- | --- |
| Ingredients | Amount (% w/w) |
| Amodimethicone | 0.50 |
| Xanthan gum | 0.40 |
| Trideceth-12 | 0.25 |
| Phenoxyethanol | 0.25 |
| Chlorophenesin | 0.25 |
| Dehydroacetic acid | 0.25 |
| Polyquaternium-80 | 0.20 |
| Glycerine | 0.10 |
| Polyquaternium-7 | 0.08 |
| Water | 63.75 |

Example 2

Dyeing test 2.1—Dyeing method

The cream described in Example 1 above is used to dye dehydrated hair sensitized by repeated oxidation streaks and dyes, which can no longer retain the dyes due to its porosity (FIG. 1).

The application of the composition according to the invention is carried out according to the following protocol.

Step 1: Applying the dyeing cream directly to dry hair

The ready-to-use composition according to the invention is applied directly to dry hair, as a treatment to the entire hair from root to tip.

The composition is then left to act for 15 minutes.

Step 2: Rinsing

The entire hair is rinsed and a conventional shampoo free of sodium lauryl ether sulfate (i.e.

Sodium Laureth Sulfate) is applied.

The shampoo is then rinsed off and a conventional detangling balm is applied.

Step 3: Hairstyling

The hair is then styled in a conventional manner.

2.2—Obtained results

The hair is dyed in a deep and extremely shiny shade. It is noticed that, during hairstyling the hair is very soft and silky because it does not show any trace of sensitization. A dyed hair is thus obtained simply without having to resort to any oxidation (FIG. 2).

Microscopic analysis of a hair after treatment reveals an intact cuticle, without any trace of corrosion in the fatty cells of the cortex. The fiber is completely healthy and intensely dyed (FIG. 3).

In addition, the effects observed are long-lasting: around two months, namely a period comparable to that of an oxidation dye.

Example 3

Instant dye transfer test 3.1—Instant dye transfer method

The cream described in Example 1 above is used to proceed with the instant transfer of dye to hair in order to carry out wicking work. A photo taken before treatment shows the hair in its natural state (FIG. 4).

The application of the composition according to the invention is carried out according to the following protocol.

Step 1: Applying the dyeing cream directly to dry hair

The ready-to-use composition according to the invention is applied directly to the selected lock of dry hair.

Then, low temperature iron at 55 degrees is slid on the strand soaked with dyeing cream (FIG. 5). The lock of hair is dyed instantly.

Step 2: Rinsing

The entire hair is rinsed and a conventional shampoo free of sodium lauryl ether sulfate (i.e.

Sodium Laureth Sulfate) is applied.

The shampoo is then rinsed off and a conventional detangling balm is applied.

Step 3: Hairstyling

The hair is then styled in a conventional manner.

3.2—Obtained results

The hair has been highlighted. During hairstyling, It is also noticed that the hair is very soft and silky because it does not show any trace of sensitization. This gives hair that is highlighted in record time, without having to resort to any oxidation and without dwell time (FIG. 6).

In addition, the effects observed are long-lasting: around two months, namely a period comparable to that of an oxidation dyeing.

Example 4

Comparative tests 4.1—Tested dyeing creams

The dyeing power of a dyeing cream similar to that described in Example 1 above but free from amino acids and whose composition is reported in Table 2 below (hereinafter "Cream ref.") was compared with dyeing power of the cream described in Example 1.

TABLE 2

Dyeing cream free from amino acids

| Ingredients | Amount (% w/w) |
| --- | --- |
| Hydrolyzed keratin (protein) | 1.50 |
| Hydrolyzed elastin (protein) | 1.30 |
| Hydrolyzed collagen (protein) | 0.90 |
| Cetearyl alcohol (alcohol) | 4.5 |
| Benzyl alcohol (alcohol) | 1.67 |
| Potassium alum (mineral powder) | 2.00 |
| Matricaria chamomile oil (vegetable oil) | 2.00 |
| Babassu oil (vegetable oil) | 1.00 |
| Wheat germ oil (vegetable oil) | 2.00 |
| Basic red 51 (cationic dye) | 2.59 |
| Titanium dioxide (mineral pigment) | 0.50 |
| Mica powder (mineral pigment) | 0.06 |
| Shea Butter | 4.00 |
| Cetrimonium chloride | 6.85 |
| Decyl glucoside | 1.00 |
| Propylene glycol | 1.00 |
| Guar hydroxypropyltrimonium chloride | 1.00 |
| Behentrimonium methosulfate | 0.50 |
| Amodimethicone | 0.50 |
| Xanthan gum | 0.40 |
| Trideceth-12 | 0.25 |
| Phenoxyethanol | 0.25 |
| Chlorophenesin | 0.25 |
| Dehydroacetic acid | 0.25 |
| Polyquaternium-80 | 0.20 |
| Glycerine | 0.10 |
| Polyquaternium-7 | 0.08 |
| Water | 63.35 |

4.2—Dyeing method

The cream described in Example 1 above and the Cream ref. are used in order to dye dehydrated and sensitized hair by repeated oxidation dyeing and strands, which can no longer retain the dyes due to its porosity.

The application of the compositions is carried out according to the protocol described in Example 2 above (see 2.1).

4.3—Obtained results

The hair treated with the cream described in Example 1 above is dyed in a deep and extremely shiny dye. It is noticed that, during hairstyling, hair is very soft and silky because it does not show any trace of sensitization. A dyed hair is thus obtained simply without having to resort to any oxidation (FIG. 7).

In addition, the effects observed are long-lasting: around two months, a period comparable to that of an oxidation dyeing.

On the contrary, hair treated with Cream ref. free from amino acids shows very faint dye without any shine. The dyes are not fixed on the skin surface and wear off very quickly with the first shampoo. It is also noticed that the hair structure is more difficult to handle (FIG. 8).

The invention claimed is:

1. A method for hair dyeing without use of an oxidation phase in a basic medium, aromatic diamine, diphenol, or ammonia, comprising applying to the hair a composition comprising:
    a proteinogenic amino acid selected from the group consisting of aspartic acid, glutamic acid, asparagine, carnitine, cysteine, glutamine, histidine, leucine, isoleucine, methionine, N-phenylalanine, proline, hydroxyproline, threonine, tryptophan, tyrosine, valine, glycine, alanine, serine, beta alanine, taurine, lysine, arginine, and a salt thereof, acid or base, organic or inorganic;
    a protein;
    an alcohol;
    a mineral powder;
    a vegetable oil; and
    a dye or a pigment.

2. The method according to claim 1, wherein the amino acid is selected from the group consisting of aspartic acid, glutamic acid, asparagine, carnitine, cysteine, glutamine, histidine, methionine, proline, hydroxyproline, tyrosine, glycine, alanine, serine, beta alanine, taurine, and arginine.

3. The method according to claim 2, wherein the amino acid is selected from the group consisting of aspartic acid, glutamic acid, cysteine, and arginine.

4. The method according to claim 1, wherein the composition contains from 0.1% to 20% of amino acid.

5. The method according to claim 1, wherein the protein is selected from the group consisting of optionally hydrolyzed creatine, optionally hydrolyzed keratin, optionally hydrolyzed wheat protein, optionally hydrolyzed silk protein, optionally hydrolyzed vegetable keratin, optionally hydrolyzed soy protein, optionally hydrolyzed collagen, optionally hydrolyzed elastin, optionally hydrolyzed pea protein, optionally hydrolyzed rice protein, optionally hydrolyzed conchioline protein, and optionally hydrolyzed whey protein.

6. The method according to claim 5, wherein the protein is selected from the group consisting of optionally hydrolyzed creatine, optionally hydrolyzed keratin, optionally hydrolyzed silk protein, optionally hydrolyzed vegetable keratin, optionally hydrolyzed soy protein, optionally hydrolyzed collagen, optionally hydrolyzed elastin, optionally hydrolyzed pea protein, optionally hydrolyzed rice protein, optionally hydrolyzed conchiolin protein, and optionally hydrolyzed whey protein.

7. The method according to claim 6, wherein the protein is selected from the group consisting of creatine, keratin, optionally hydrolyzed wheat protein, optionally hydrolyzed silk protein, and optionally hydrolyzed soy protein.

8. The method according to claim 1, wherein the composition contains 0.1% to 20% of protein.

9. The method according to claim 1, wherein the alcohol is selected from the group consisting of butanol, isopropanol, ethanol, and benzyl alcohol.

10. The method according to claim 1, wherein the composition contains 0.5% to 20% of alcohol.

11. The method according to claim 1, wherein the vegetable oil is selected from the group consisting of sweet almond oil, olive oil, argan oil, chamomile oil, roman chamomile oil, Haarlem oil, babassu oil, broccoli oil, avocado oil, linseed oil, apricot oil, cucumber oil, black seed oil, brazil nut oil, grape seed oil, shea olein, sesame oil, and tomato oil.

12. The method according to claim 11, wherein the vegetable oil is selected as being matricaria chamomile oil or roman chamomile oil.

13. The method according to claim 1, wherein the mineral powder is selected from the group consisting of kaolin powder, tartaric acid powder, alum powder, calcium carbonate powder, potassium carbonate powder, tara powder, titanium oxalate, and magnesium powder.

14. The method according to claim 13, wherein the mineral powder is selected as being alum powder or tartaric acid powder.

15. The method according to claim 1, comprising the following steps:
applying the composition to the hair;
leaving to act for a period from 5 minutes to 30 minutes; and
rinsing the hair with water.

16. The method according to claim 1, wherein the method is conducted without the use of hydrogen peroxide, a base, or a coupler.

17. The method according to claim 1, wherein the method is conducted in a medium with an acidic pH of 5.5.

* * * * *